United States Patent [19]
Drivon et al.

[11] Patent Number: 5,994,600
[45] Date of Patent: Nov. 30, 1999

[54] METHOD FOR PREPARING α,ω-BROMOCHLOROALKANES

[75] Inventors: Gilles Drivon, Saint-Martin-en-Haut; Christophe Ruppin, Pierre-Bènite, both of France

[73] Assignee: Elf Atochem S.A., Cedex, France

[21] Appl. No.: 08/981,960

[22] PCT Filed: Jul. 2, 1996

[86] PCT No.: PCT/FR96/01027

§ 371 Date: Apr. 2, 1998

§ 102(e) Date: Apr. 2, 1998

[87] PCT Pub. No.: WO97/03036

PCT Pub. Date: Jan. 30, 1997

[30] Foreign Application Priority Data

Jul. 11, 1995 [FR] France .................................. 95 08360

[51] Int. Cl.$^6$ ...................................................... C07C 19/00
[52] U.S. Cl. ................................................................ 570/259
[58] Field of Search ............................................... 570/259

[56] References Cited

U.S. PATENT DOCUMENTS 2,839,574  6/1958  Servigne et al. ......................... 570/259
2,868,850  1/1959  Servigne et al. ......................... 570/259

*Primary Examiner*—Alan Siegel
*Attorney, Agent, or Firm*—Miller, White, Zelano, & Branigan, P.C.

[57] ABSTRACT

To prepare α,ω-bromochloroalkanes, a cyclic ether, to which water has optionally been added, is hydrochlorinated and then the resultant phase is reacted, without any prior purification or separation, with gaseous hydrobromic acid.

15 Claims, No Drawings

METHOD FOR PREPARING α,ω-BROMOCHLOROALKANES

This application is a 371 of PCT/FR96/01027 filed Jul. 2, 1996.

FIELD OF THE INVENTION

The present invention relates to a process for the direct preparation of α,ω-bromochloroalkanes from cyclic ethers.

BACKGROUND OF THE INVENTION

Haloalkanes, and more particularly α,ω-bromochloroalkanes, are widely used as starting materials for the preparation of pharmaceutical, pesticidal and detergent products.

Many methods have been described for producing these α,ω-bromochloroalkanes.

They most often involve the reaction of halogens (bromine or chlorine) or of their derivatives, such as $PBr_3$ or $SBr_6$, with an α,ω-chlorohydroxyalkane or alternatively the reaction of halogens (bromine or chlorine) or of their derivatives, such as $SOCl_2$, with a haloalkane or an ω-haloalkanoic acid.

British Patent 788,349 describes a process for the preparation of 1-bromo-4-chlorobutane which consists in treating, in a first stage, THF with dry hydrochloric acid in the presence of traces of $ZnCl_2$ at a temperature which reaches approximately 100° C. and then, in a second stage, in treating the 4-chloro-1-butanol obtained above with red phosphorus and then with dry bromine at a temperature of between 0° C. and −10° C. The 1-bromo-4-chlorobutane is obtained with a yield of approximately 62% with respect to the THF used.

U.S. Pat. No. 2,839,574 mentions a process for the preparation of 1-bromo-4-chlorobutane which avoids the use of red phosphorus and of bromine or of SBr6. This process consists in treating predistilled 4-chloro-1-butanol with dry gaseous hydrobromic acid in the presence of a solvent at boiling point which forms an azeotrope with the water formed according to the reaction:

$$Cl(CH_2)_4OH + HBr \rightarrow Br(CH_2)_4Cl + H_2O.$$

The yield is approximately 70%.

In the Japanese patent application published under No. JP 5791930, the 1-bromo-4-chlorobutane was obtained with a yield of approximately 90% by treating freshly distilled 4-chloro-1-butanol with $SBr_6$ formed from sulphur and bromine, according to the reaction scheme:

$$SBr_6 + 6Cl(CH_2)_4OH \rightarrow 6Br(CH_2)_4Cl + H_2SO_4 + 2H_2O$$

In the case where $SBr_6$ is reacted with an unpurified 4-chloro-1-butanol, arising in particular from a mixture of tetrahydrofuran and hydrochloric acid, the 1-bromo-4-chlorobutane yield is approximately 70%.

D.C. Sayles and Ed. F. Degering (Journal of American Chemistry Society, 71, page 3162, 1949) describe a method for the preparation of 1-bromo-4-chlorobutane by treating n-bromobutane with sulphuryl chloride ($SO_2Cl_2$) in the presence of benzoyl peroxide, at reflux of the reactants. The 1-bromo-4-chlorobutane yield is 35%.

Smushkevich, Yu.I et al. apply the Borodin-Hunsdiecker reaction to ω-chloroalkanoic acids (Tr. Mosk. Khim. Technol. Inst. No. 61, pp 47–48, 1969).

They thus obtain α,ω-bromochloroalkanes by treating ω-chloroalkanoic acids with HgO and bromine in $CCl_4$ medium according to the reaction scheme:

$$Cl(CH_2)_nCOOH + Br_2 \rightarrow Cl(CH_2)_nBr + CO_2 + HBr$$

It should also be reported that Hahn, Roger C. (Journal of Organic Chemistry, 53 (6), pp. 1331–3, 1988) describes a method for the preparation of α,ω-bromochloroalkanes by a halogen exchange reaction. Thus, 1-bromo-6-chlorohexane is obtained by heating a mixture of n-bromobutane and 1,6-dichlorohexane in the presence of tetrabutylammonium bromide according to the reaction scheme:

$$Br(CH_2)_3CH_3 + Cl(CH_2)_6Cl \rightarrow Br(CH_2)_6Cl + Cl(CH_2)_3CH_3$$

All these methods have many disadvantages. They use starting compounds which are often impure, requiring purification operations, and reactants which are expensive and difficult to handle (P+bromine, S+bromine).

The α,ω-bromochloroalkane yields are low and the products obtained contain impurities, the removal of which results in difficult and expensive separation operations.

SUMMARY OF THE INVENTION

A process has now been found for the direct preparation of α,ω-bromochloroalkane of formula $Br(CH_2)_nCl$ (I) in which n represents an integer ranging from 3 to 8, from a cyclic ether of formula $$\underset{O}{\underset{|}{(CH_2)_n}}$$

(II) in which n has the same as in meaning formula (I), characterized in that:

a) the said cyclic ether (II), optionally with an amount of water added at most equal to 20 parts by weight per 100 parts by weight of cyclic ether (II), is brought into contact with gaseous hydrochloric acid and then b) the above phase obtained in a) is brought into contact with gaseous hydrobromic acid.

According to the present invention, the amount of water added to the cyclic ether (II) is between 1 part and 15 parts by weight per 100 parts by weight of cyclic ether (II) used and preferably an amount between 5 and 10 parts by weight.

It would not be departing from the scope of the invention if the stage a) were carried out without the addition of water.

Mention may be made, as an example of a cyclic ether of formula (II) which can be used according to the present invention, of 1,3-propylene oxide (oxetane), tetrahydrofuran, tetrahydropyran, 1,6-hexamethylene oxide (oxepane) or 1,7-heptamethylene oxide (oxocane).

The process of the present invention applies very particularly to the preparation of 1-bromo-4-chlorobutane from tetrahydrofuran.

According to the present invention, it is not necessary to isolate and/or to purify the α,ω-chlorohydroxyalkane (III) obtained in a) by hydrochlorination of the cyclic ether (II) according to the the reaction scheme:

A $$\underset{(II)}{\underset{O}{\underset{|}{(CH_2)_n}}} + HCl\ gas \longrightarrow HO(CH_2)_nCl \quad (III)$$

The stage b) is carried out by directly reacting the above phase obtained in a), containing the intermediate (III), with gaseous hydrobromic acid to result in the α,ω-bromochloroalkane (I) according to the reaction scheme:

$$HO(CH_2)_nCl + HBr \text{ gas} \xrightarrow{B} Br(CH_2)_nCl + H_2O$$
$$(III) \quad\quad\quad\quad\quad\quad\quad (I)$$

One of the advantages of the invention is clearly apparent here; it is not necessary to isolate and to purify the intermediate α,ω-chlorohydroxyalkane (III) obtained in a) before reacting it with gaseous hydrobromic acid (stage b)).

The stages a) and b) of the process according to the invention are carried out at a temperature ranging from room temperature (approximately 20° C.) to approximately 100° C. and preferably at a temperature ranging from 40° C. to 70° C.

According to the present invention, the temperatures can be identical or different in the two stages but it is preferable to operate at a single temperature.

According to the present invention, the stage a) is carried out with a gaseous HCl/cyclic ether molar ratio of between 1 and 3 and preferably between 1.10 and 2 and the stage b) is carried out with a gaseous HBr/cyclic ether molar ratio of between 1 and 2 and preferably between 1.20 and 1.60.

The duration of the reaction for each of the stages a) and b) can vary within wide limits but it is generally between 2 and 30 hours and preferably between 10 and 25 hours.

The reaction can be carried out at atmospheric pressure.

According to the present invention, gaseous hydrochloric acid is introduced into the cyclic ether, to which water has optionally been added, and then, on completion of the introduction, the reaction is continued by directly introducing gaseous hydrobromic acid into the reaction mixture obtained above.

On completion of the introduction of HBr gas, the water formed is removed by settling the reaction mixture and then the α,ω-bromochloroalkane is purified, in particular by distillation under reduced pressure.

The preparation of α,ω-bromochloroalkane according to the process of the invention has the advantage of being carried out in two successive reaction stages in the same equipment without any purification or separation of the intermediate α,ω-chlorohydroxyalkane.

The process of the invention also has the advantage of being carried out without a solvent and in the absence of a catalyst.

The α,ω-bromochloroalkane yields are high and the products obtained can be easily purified. In certain cases, their purity is such as to enable them to be used as is.

The examples which follow illustrate the invention.

EXAMPLE 1

Stage a 325 g (4.5 mol) of tetrahydrofuran and 16.2 g of water (5% by weight) are introduced, under an inert atmosphere, into a 1-liter glass reactor equipped with a mechanical stirrer (anchor), a temperature probe and a gas injection tube and surmounted by a glycol/water-cooled condenser (temperature approximately −20° C.).

The whole assembly is heated to 55° C. and then, over 14 h, 255 g (7 mol) of HCl gas are injected at a decreasing flow rate ranging from 1.5 mol/h to 0.15 mol/h, while maintaining the temperature of the reaction mixture at 60° C.

On completion of the HCl introduction, the crude reaction mixture (593 g) contains 2.7% of water, 14% of HCl, 76.5% of 4-chloro-1-butanol, 3% of 1,4-dichlorobutane and 1.5% of residual THF. Thus, the conversion of the THF is greater than 97% and the 4-chloro-1-butanol crude molar yield is approximately 93% with respect to the THF used.

Stage b

After cooling to 50° C., 567 g (7 mol) of gaseous HBr are injected directly into the reaction mixture a) obtained above with stirring over 20 h with a decreasing flow rate ranging from 0.75 mol/h to 0.15 mol/h. During the introduction of the HBr, the HCl dissolved above degasses from the reaction mixture. The progress of the reaction is monitored by gas phase chromatographic analysis (GPC).

On completion of the introduction of the HBr, after cooling to room temperature and stopping the stirring, the reaction mixture settles out. 280 g of a yellowish aqueous phase containing 58% of HBr and 728 g of a colourless organic phase are obtained, the organic phase comprising 91% of 1-bromo-4-chlorobutane, 2.8% of 1,4-dichlorobutane, 5.8% of 1,4-dibromobutane and 0.1% of residual 4-chloro-1-butanol, resulting in a 1-bromo-4-chlorobutane crude molar yield of 92.5% with respect to the 4-chloro-1-butanol and of 86% with respect to the THF used.

The 1-bromo-4-chlorobutane is then purified by distillation under reduced pressure (30 mm Hg) with an adiabatic column containing 20 theoretical plates. After drawing off a top fraction comprising the residual 4-chloro-1-butanol and the 1,4-dichlorobutane, 584 g of 1-bromo-4-chlorobutane are distilled with a purity, determined by GPC, of 99.3%, i.e. with a distillation yield of 87.5%. The result is a distilled 1-bromo-4-chlorobutane molar yield of the order of 75% with respect to the THF used (B.P.$_{30 \ mm \ Hg}$=83.5° C.).

EXAMPLE 2

Stage a 325 g of tetrahydrofuran and 16.2 g of water are introduced into the same equipment as for Example 1. The whole assembly is heated to 50° C., with stirring, and then 365 g of HCl gas are injected over 25 h at a flow rate from 1.5 mol/h to 0.35 mol/h, while maintaining the temperature of the reaction mixture at 50° C.

586.5 g of a crude reaction mixture are then obtained, which reaction mixture contains 2.8% of water, 12.5% of HCl, 78.5% of 4-chloro-1-butanol, 2% of 1,4-dichlorobutane and 1.7% of residual THF. The result is a conversion of the THF of the order of 97% and a 4-chloro-1-butanol crude molar yield of 94% with respect to the starting THF.

Stage b 6.9 mol of HBr gas are then directly injected into this reaction mixture at 50° C. over 18 h 30 at a flow rate from 0.7 mol/h to 0.15 mol/h. After settling and separation, 273 g of an acidic aqueous phase and 747 g of an organic phase are obtained, the organic phase comprising 2.2% of 1,4-dichlorobutane, 5.5% of 1,4-dibromobutane and 92.1% of 1-bromo-4-chlorobutane. The result is a 1-bromo-4-chlorobutane crude molar yield of 94.5% with respect to the 4-chloro-1-butanol and of 89% with respect to the THF used.

EXAMPLE 3

The preparation is carried out in the same equipment and according to the same conditions as in Example 1, except that the stage a) is carried out without the addition of water. On completion of the introduction of gaseous HCl, conversion of the THF is 85% and the 4-chloro-1-butanol crude molar yield is approximately 82%.

EXAMPLE 4

(Comparative Example)

108 g of tetrahydrofuran (1.5 mol) and 444 g (4.5 mol) of a 37% aqueous HCl solution are introduced into the same equipment as in Example 1. After heating, with stirring, at 65–70° C. for 5 h, conversion of the THF to 4-chloro-1-butanol is 78%. After heating for an additional 6 h, conversion of the THF to 4-chloro-1-butanol remains below 82%.

Under the conditions of this example, the second stage of synthesis of the 1-bromo-4-chlorobutane first requires a stage of separation of the aqueous phase and then a stage of purification of the crude intermediate 4-chloro-1-butanol, in order to avoid the excessive formation of 1,4-dibromobutane from the residual THF.

We claim:

1. A process for the direct preparation of $\alpha,\omega$-bromochloroalkane of formula $Br(CH_2)_nCl$ (I) in which n represents an integer ranging from 3 to 8, from a cyclic ether of formula

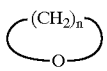

(II) in which n has the same meaning as in the formula (I), characterized in that:
   a) the said cyclic ether (II), having an amount of water added between 1 part and 15 parts by weight per 100 parts by weight of cyclic ether (II), is brought into contact with gaseous hydrochloric acid and then
   b) the resultant phase obtained in a) is directly brought into contact with a reactant consisting essentially of gaseous hydrobromic acid.

2. A process according to claim 1, characterized in that the cyclic ether (II) is tetrahydrofuran.

3. A process according to claim 1, characterized in that the amount of water added to the ether (II) is between 5 and 10 parts by weight per 100 parts by weight of cyclic ether (II) used.

4. A process according claim 1, to characterized in that, in the stage a), the gaseous HCl/cyclic ether molar ratio is between 1 and 3 and in that, in the stage b), the gaseous HBr/cyclic ether molar ratio is between 1 and 2.

5. A process according to claim 4, characterized in that the gaseous HCl/cyclic ether molar ratio is between 1.10 and 2 and in that the gaseous HBr/cyclic ether molar ratio is between 1.20 and 1.60.

6. A process according to claim 1, characterized in that the stages a) and b) are carried out at a temperature ranging from room temperature to approximately 100° C.

7. A process according to claim 6, characterized in that the stages a) and b) are carried out at a temperature ranging from 40° C. to 70° C.

8. A process according to claim 3, characterized in that the cyclic ether (II) is tetrahydrofuran.

9. A process according to claim 5, characterized in that the cyclic ether (II) is tetrahydrofuran.

10. A process according to claim 7, characterized in that the cyclic ether (II) is tetrahydrofuran.

11. A process according to claim 8, characterized in that, in the stage a), the gaseous HCl/cyclic ether molar ratio is between 1 and 3 and in that, in the stage b), the gaseous HBr/cyclic ether molar ratio is between 1 and 2.

12. A process according to claim 11, characterized in that the gaseous HCl/cyclic ether molar ratio is between 1.10 and 2 and in that the gaseous HBr/cyclic ether molar ratio is between 1.20 and 1.60.

13. A process according to claim 11, characterized in that the stages a) and b) are carried out at a temperature ranging from room temperature to approximately 100° C.

14. A process according to claim 12, characterized in that the stages a) and b) are carried out at a temperature ranging from 40° C. to 70° C.

15. A process according to claim 1, wherein the process is conducted without a catalyst.

* * * * *